(12) United States Patent
Hawkins et al.

(10) Patent No.: US 8,480,628 B2
(45) Date of Patent: Jul. 9, 2013

(54) INTRODUCER APPARATUS

(75) Inventors: M. Kem Hawkins, Bloomington, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1862 days.

(21) Appl. No.: 11/294,912

(22) Filed: Dec. 6, 2005

(65) Prior Publication Data

US 2006/0135973 A1 Jun. 22, 2006

Related U.S. Application Data

(60) Provisional application No. 60/633,799, filed on Dec. 7, 2004.

(51) Int. Cl.
*A61M 5/178* (2006.01)
(52) U.S. Cl.
USPC ..................... 604/170; 604/164.01
(58) Field of Classification Search
USPC .............. 604/164.01–170.03, 158–163
See application file for complete search history.

(56) References Cited

U.S. PATENT DOCUMENTS

| | | | |
|---|---|---|---|
| 4,650,472 A | | 3/1987 | Bates |
| 4,840,622 A | | 6/1989 | Hardy |
| 4,895,564 A * | | 1/1990 | Farrell ................. 604/164.1 |
| 5,489,269 A | | 2/1996 | Aldrich et al. |
| 5,683,370 A * | | 11/1997 | Luther et al. ............. 604/528 |
| 6,500,157 B2 * | | 12/2002 | Luther .................. 604/264 |
| 2004/0073163 A1 | | 4/2004 | Tomaschko et al. |

FOREIGN PATENT DOCUMENTS

| | | |
|---|---|---|
| DE | 198 16 986 C1 | 8/1999 |
| EP | 0 555 088 A2 | 8/1993 |
| EP | 1 084 728 A1 | 3/2001 |
| WO | WO 2005/004967 A2 | 1/2005 |

OTHER PUBLICATIONS

Cook Incorporated, "Micropuncture," Brochure MPIS998, Sep. 1998, 8 pgs.

* cited by examiner

*Primary Examiner* — Kevin C Sirmons
*Assistant Examiner* — Phillip Gray
(74) *Attorney, Agent, or Firm* — Brinks Hofer Gilson & Lione

(57) ABSTRACT

An apparatus for providing percutaneous access to a vessel of a patient over a wire guide. An outer sleeve of the apparatus has proximal and distal open ends, and has a lumen extending longitudinally therethrough. An inner sleeve has proximal and distal open ends, and has a lumen extending longitudinally therethrough. The inner sleeve is sized to be received within the lumen of the outer sleeve. The inner sleeve has a main body portion having a distal portion that tapers toward its distal open end. The tapered distal portion extends distal to the distal open end of the outer sleeve to provide a generally smooth diametrical transition between the outer sleeve and the wire guide. A more rigid stiffening cannula has proximal and distal open ends, and has a lumen extending longitudinally therethrough. The lumen of the stiffening cannula is sized to receive the wire guide therethrough. The stiffening cannula is sized to be received within the lumen of the inner sleeve, and extends along the main body portion of the inner sleeve to a terminal point proximal to the inner sleeve distal end. The stiffening cannula and the inner sleeve are engaged such that relative axial movement between them is substantially inhibited. As a result, the inner sleeve distal portion acts as a shield for the distal end of the stiffening cannula distal end when the apparatus is percutaneously introduced into the vessel.

14 Claims, 5 Drawing Sheets

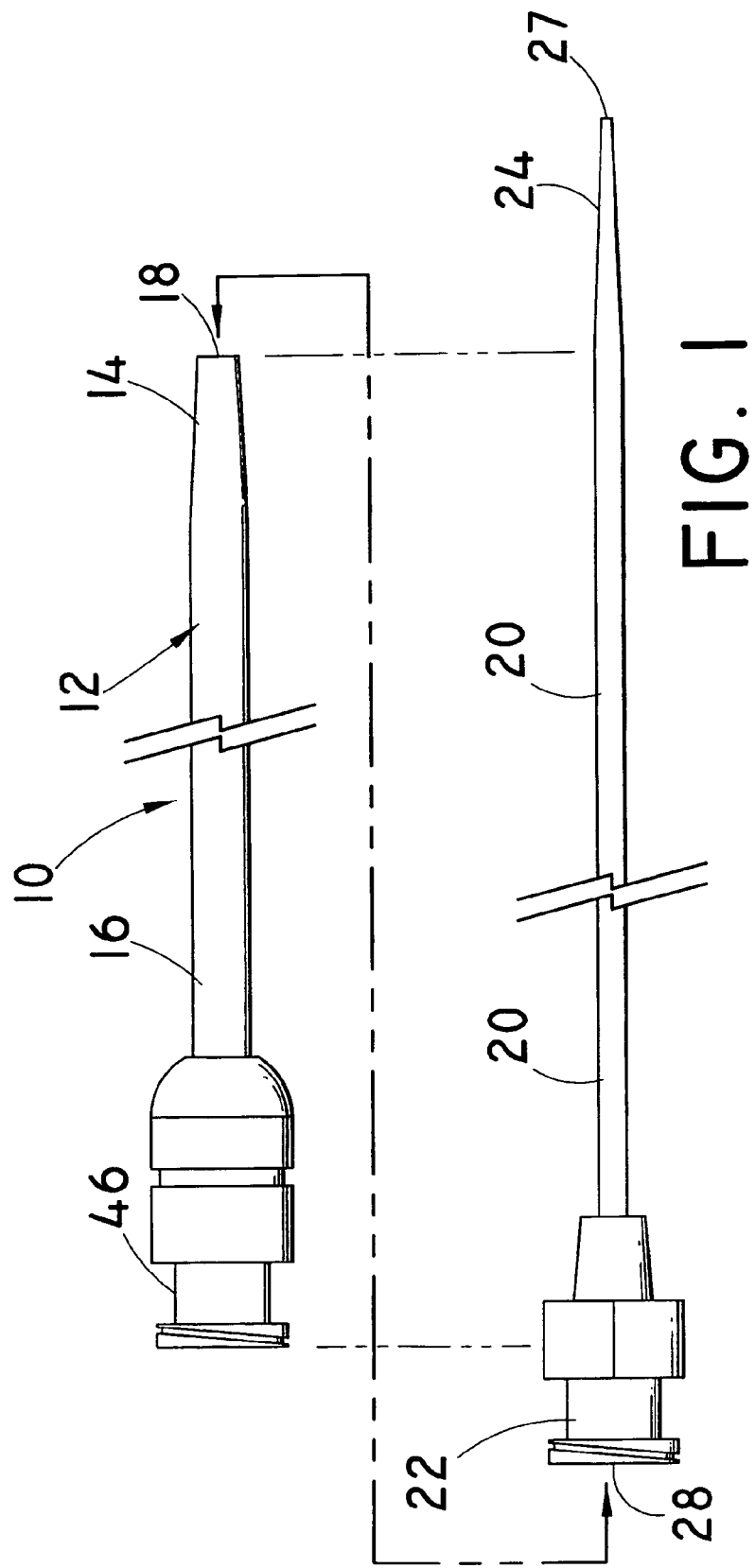

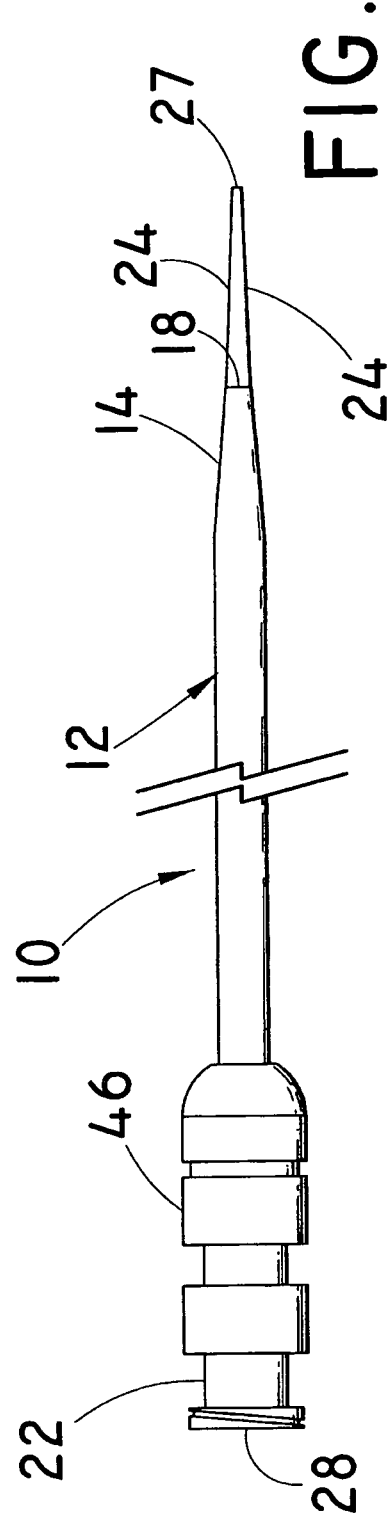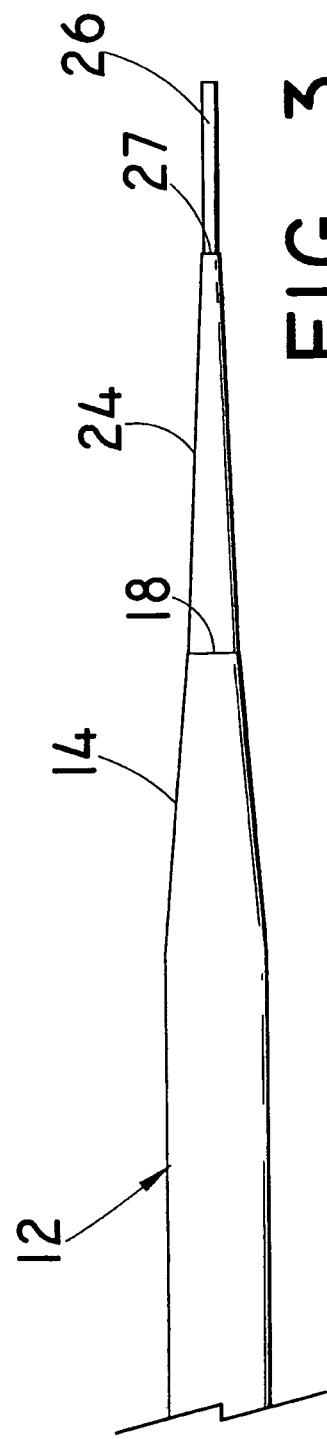

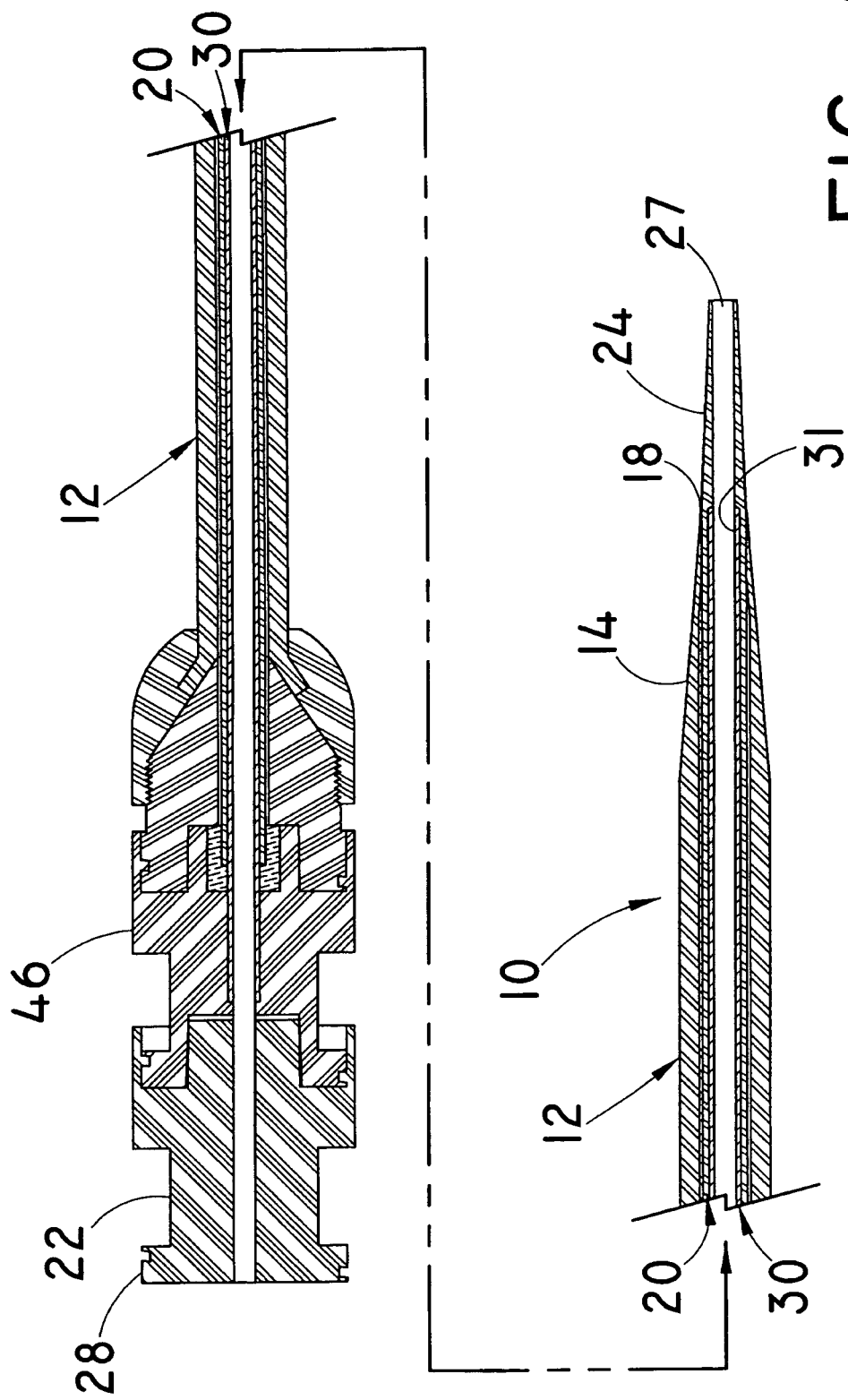

INTRODUCER APPARATUS

RELATED APPLICATION

The present patent document claims the benefit of the filing date under 35 U.S.C. §119(e) of Provisional U.S. Patent Application Ser. No. 60/633,799, filed Dec. 7, 2004, which is hereby incorporated by reference.

BACKGROUND

1. Technical Field

This invention relates to the field of percutaneous access to the vascular system. More specifically, this invention relates to an apparatus and system for percutaneous access to a vessel of a patient when initial entry is made with a small gauge needle.

2. Background Information

Many medical procedures require the percutaneous placement of an interventional medical device, such as a catheter, into an artery or vein. Among others, such interventional devices may be used in connection with blood pressure monitoring, blood sampling, and the administration of drugs and fluids to a patient.

Typically, such devices are introduced using the well-known Seldinger technique. The Seldinger technique for percutaneous entry into the vascular system has been in widespread use in diagnostic and interventional medicine for many years. In the Seldinger technique, the physician makes an oblique entry into the artery or vein with a beveled needle. A wire guide is introduced into the proximal end of the needle, and passes through the length of the needle into the artery or vein. The needle is thereafter withdrawn, leaving the wire guide in place. The catheter or other interventional device is then passed over the wire guide, through the puncture, and into the artery or vein at the needle puncture site. Once the catheter is in place, the wire guide may be withdrawn.

One of the disadvantages of this procedure is that the initial needle stick must normally be made with a needle that is large enough to accept the wire guide through its central bore. Conventional wire guides are often comprised of a tightly wound helical stainless steel wire coil. In order to have sufficient rigidity to properly support and lead many standard catheters and other interventional devices, such wire guides are typically constructed to have an outer diameter in the range of about 0.035 to 0.038 inch (0.89 to 0.97 mm). A wire guide having this diameter will pass through an 18 gauge thinwall needle. An 18 gauge needle typically has a 0.050 inch (1.27 mm) outer diameter and a 0.042 inch (1.07 mm) inner diameter (I.D.).

The 18 gauge needle is the most commonly used needle for initial vascular access, and has become the standard needle for use with the Seldinger technique for percutaneous catheterization. However, the outer diameter of an 18 gauge needle is just large enough to damage tissue or cause excessive bleeding if it does not enter the vessel correctly, or if it inadvertently penetrates some other organ. As a result, it is desirable to utilize a smaller gauge needle to effect the initial entry. Smaller needles such as 21 gauge thin wall down to 24 gauge thin wall are considered small enough so as not to cause damage to tissue or organs, or cause excessive bleeding if inserted off target. A 21 gauge thin wall needle typically has a 0.032 inch (0.81 mm) outer diameter (O.D.) and a 0.022 inch (0.55 mm) inner diameter (I.D.). A 24 gauge thin wall needle typically has a 0.022 inch (0.55 mm) O.D., and a 0.014 inch (0.35 mm) I.D.

In addition to their smaller diameters, smaller gauge needles typically have a correspondingly shorter bevel at the needle tip compared to the lengthier bevel tip of an 18 gauge needle. It is much easier to get a short bevel into the lumen of a small vessel than the longer bevel of the type found in an 18 gauge needle. However, the respective bores of smaller needles, such as 21 to 24 gauge needles, are not large enough to pass a standard 0.035 inch or 0.038 inch (0.89 mm or 0.97 mm) diameter wire guide therethrough. Generally a wire guide of 0.018 inch, or smaller, is required to pass through the bore of such small diameter needles. However, as stated, many diagnostic and interventional devices require at least a 0.035 inch (0.89 mm), and more preferably a 0.038 inch (0.97 mm), diameter wire for optimal introduction and manipulation through the vasculature.

U.S. Pat. No. 4,650,472, assigned to the assignee herein, discloses a catheterization apparatus which allows a smaller gauge needle, such as a 22 gauge needle, to be used for the initial puncture through the skin of the patient in place of the conventional 18 gauge needle. A 22 gauge needle typically has a 0.028 inch (0.71 mm) O.D. and a 0.019 inch (0.48 mm) I.D. This patent is incorporated by reference herein. A 0.018 inch (0.46 mm) outer diameter wire guide is inserted through the bore of the 22 gauge needle. In the apparatus described in the patent, a removable inner sleeve is provided over the wire guide but inside the outer sleeve portion of the apparatus. This removable inner sleeve has a tapered tip which extends through the distal opening of the outer sleeve, and provides a smooth diametrical transition between the large distal opening of the outer sleeve and the 0.018 inch wire guide. The inner sleeve is generally about 0.038 inch (0.97 mm) O.D., and the outer sleeve is tapered to fit over the inner sleeve. The outer sleeve and the inner sleeve are inserted into the blood vessel in tandem. The smooth diametrical transition of the leading end of this tandem minimizes the trauma that may otherwise be caused by the insertion of the large diameter outer sleeve over the small diameter wire guide. Once the outer sleeve is properly positioned within the blood vessel, the inner sleeve and the smaller wire guide can be withdrawn, leaving the outer sleeve in place. If desired, a larger (0.035 to 0.038 inch) (0.89 to 0.97 mm) wire guide can then be introduced through the outer sleeve and into the vessel. The outer sleeve can thereafter be removed from the patient, leaving the larger wire guide in the vessel ready to accept a catheter or other interventional device, as in the standard Seldinger technique. An example of such an introducer system is the MICROPUNCTURE® introducer set, available from Cook Incorporated, of Bloomington, Ind.

The apparatus disclosed in the '472 patent has been successfully used to percutaneously insert a catheter into a blood vessel using a wire guide and an introducer needle which are much smaller in diameter than the distal opening of the catheter. This ensures good flow characteristics for the catheter and a minimum of tissue trauma to the patient. It also allows for the introduction of larger diagnostic and interventional devices than would otherwise be possible when an initial entry is made with a small diameter needle.

In some cases when a catheter is to be inserted using a small gauge needle, such as a needle of the type described in the '472 patent, it is necessary to make the puncture through tough, fibrous tissue. Examples of such tissue are scar tissue, muscle tissue and the like. In such cases it is sometimes desired to further enhance the rigidity or column strength of the disclosed two-part dilator system, so that the apparatus can be more easily pushed through the puncture site and the vessel wall, and yet still be flexible enough so that additional trauma is not caused to the vessel wall when the device enters the vessel. In order to enhance the rigidity of the dilator system, it is known to position a stiffening cannula, such as a thin stainless hypodermic needle cannula, within the lumen of the inner sleeve of the apparatus of the '472 patent. The stiffening cannula generally extends from the proximal end of the apparatus and ends just short of the distal tip taper of the inner sleeve. Since the tip taper of the inner sleeve is not reinforced by the stiffening cannula, it thereby retains its flexibility. The stiffening cannula provides extra stiffness to the main body of the apparatus without adding significant bulk, complexity or additional parts. An example of such an introducer system is the MICROPUNCTURE® PUSH-PLUS™ introducer set, available from Cook Incorporated, of Bloomington, Ind.

The use of a stiffening cannula has worked fairly well when needles on the larger end of this system, such as 21 gauge needles, are utilized. However, as the systems get smaller (e.g., 22, 23 and 24 gauge needles), the stiffening cannula may protrude through the tapered distal end of the inner sleeve when the inner sleeve is pushed through the tough, fibrous tissue. As a result, the stiffening cannula may directly access the vessel and tissue. In this event, considerable trauma can be caused to the vessel wall and tissue due to the lack of flexibility of the hard, stiffening cannula. This can also even be a problem with some larger non-stiffened systems when they encounter scar tissue or calcifications during introduction.

There exists a need for a percutaneous insertion apparatus for an interventional device that can utilize small needles on the order of 22, 23 or 24 gauge, or smaller, for the initial insertion through the skin of the patient, and wherein the components of the system have sufficient stiffness to allow the insertion apparatus to be pushed through tough, fibrous tissue without directly exposing the tissue to trauma resulting from the use of stiff components.

BRIEF SUMMARY

The present invention addresses the aforementioned problems encountered in the prior art. One aspect of the invention comprises engaging the inner sleeve and the stiffening cannula in a manner such that relative axial movement between them is inhibited as the device is inserted through the skin of the patient. As a result, the inner sleeve cannot accordion and slide back in the proximal direction along the stiffening cannula as the system is advanced through tissue, and the distal tip of the stiffening cannula cannot protrude through the inner sleeve and into the vessel to cause trauma to the patient.

In one form thereof, the invention comprises an apparatus for providing percutaneous access to a vessel of a patient over a wire guide. An outer sleeve of the apparatus has proximal and distal open ends, and has a lumen extending longitudinally therethrough. An inner sleeve has proximal and distal open ends, and has a lumen extending longitudinally therethrough. The inner sleeve is sized to be received within the lumen of the outer sleeve. The inner sleeve has a main body portion, and has a distal portion that tapers toward the inner sleeve distal open end. The tapered distal portion extends distal to the distal open end of the outer sleeve to provide a generally smooth diametrical transition between the outer sleeve and the wire guide. A more rigid stiffening cannula disposed within the lumen of the inner sleeve has proximal and distal open ends, and has a lumen extending longitudinally therethrough. The lumen of the stiffening cannula is sized to receive the wire guide therethrough. The stiffening cannula extends along the main body portion of the inner sleeve to a terminal point, which terminal point is proximal to the inner sleeve distal end. The stiffening cannula and the inner sleeve are engaged such that relative axial movement between them is substantially inhibited, wherein the inner sleeve distal portion shields the stiffening cannula distal end when the apparatus is percutaneously introduced into the vessel.

In another form thereof, the invention comprises a method of providing access to a vessel of a patient. A small diameter wire guide is initially introduced into a vessel, which wire guide has a diameter not exceeding about 0.018 inch (0.46 mm). An introducer apparatus is provided for insertion into the vessel. The introducer apparatus comprises an outer sleeve having a lumen extending longitudinally therethrough, and having an open distal end. An inner sleeve has a lumen extending longitudinally therethrough, and has a distal portion that tapers to an open distal end. The inner sleeve is sized to be received within the lumen of the outer sleeve. The open distal end of the inner sleeve has a diameter just large enough to enable the wire guide to pass freely therethrough. The tapered distal portion provides a generally smooth diametrical transition between the distal end of the outer sleeve and the wire guide. A stiffening cannula has a lumen extending longitudinally therethrough. The lumen of the stiffening cannula is sized to receive the wire guide therethrough. The stiffening cannula is sized to be received within the lumen of the inner sleeve. The stiffening cannula and the inner sleeve are engaged such that relative axial movement between them is substantially inhibited. The tapered distal portion of the inner sleeve shields the stiffening cannula when the apparatus is introduced into the vessel. The introducer apparatus is then inserted into the vessel over the wire guide. The wire guide, inner sleeve, and stiffening cannula may then be removed from the vessel, while maintaining the outer sleeve in the vessel.

In still another form thereof, the invention comprises a system for providing percutaneous access to a vessel of a patient. The system includes a first wire guide having a first diameter, a second wire guide having a second diameter, and an introducer apparatus. The introducer apparatus comprises an outer sleeve having proximal and distal open ends, and a lumen extending longitudinally therethrough. The distal open end has a diameter substantially the same as the diameter of the second wire guide, and is sized to permit the second wire guide to pass freely therethrough. An inner sleeve of the apparatus has a lumen extending longitudinally therethrough, and has a distal portion that tapers to an open distal end. The inner sleeve is sized to be received within the lumen of the outer sleeve. The open distal end of the inner sleeve has a diameter substantially the same as the diameter of the first wire guide, and is sized to permit the first wire guide to pass freely therethrough. The apparatus includes a stiffening cannula having a lumen extending longitudinally therethrough. The lumen of the stiffening cannula is sized to receive the first wire guide therethrough, and the stiffening cannula is sized to be received within the lumen of the inner sleeve. The stiffening cannula and the inner sleeve are engaged such that relative axial movement between them is substantially inhibited, and are oriented such that the tapered distal portion of the inner sleeve shields the stiffening cannula when the apparatus is percutaneously introduced into the vessel. Optionally, the system includes a small bore needle, preferably of gauge size 22 or smaller. Preferably, the first wire guide diameter does not exceed about 0.18 inch (0.46 mm), and the second wire guide diameter is at least about 0.035 inch (0.89 mm).

BRIEF DESCRIPTION OF THE DRAWINGS

FIG. 1 is an elevational view of an outer sleeve and an inner sleeve prior to joinder in the inventive introducer apparatus;

FIG. 2 is an elevational view of the inventive apparatus, wherein the inner sleeve is received within a lumen of the outer sleeve;

FIG. 3 is an enlarged elevational view of the distal portion of the apparatus as shown in FIG. 2, and showing a wire guide extending from the distal end of the inner sleeve;

FIG. 4 is a longitudinal sectional view of the fully assembled inventive introducer apparatus, showing the inner sleeve affixed to the stiffening cannula;

DETAILED DESCRIPTION OF THE DRAWINGS AND THE PRESENTLY PREFERRED EMBODIMENTS

Figure 6:
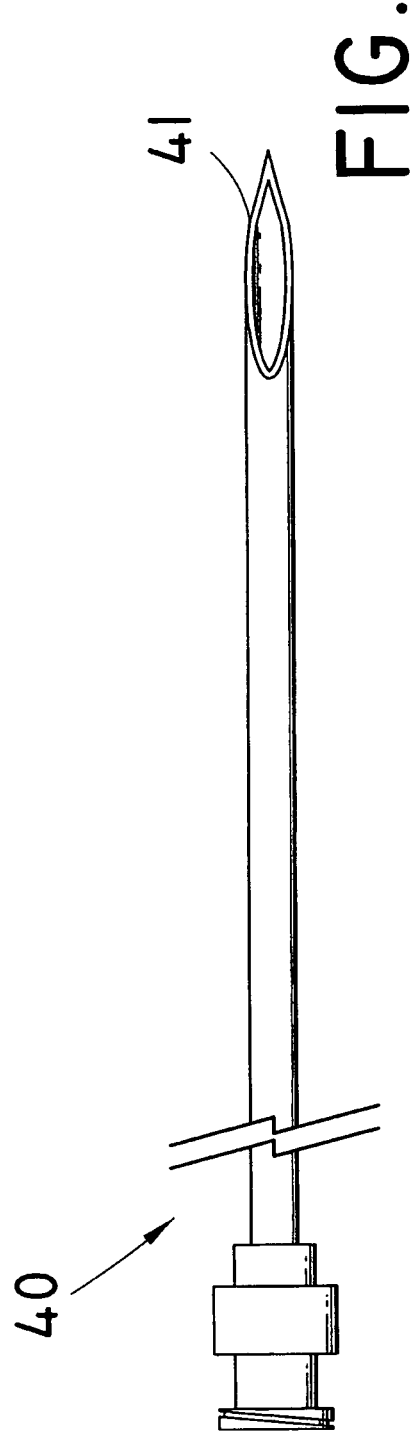
FIG. 6 illustrates one type of small gauge needle that may be used for the initial puncture.

For purposes of promoting an understanding of the present invention, reference will now be made to the embodiments illustrated in the drawings, and specific language will be used to describe the same. It is nevertheless to be understood that no limitation of the scope of the invention is thereby intended, the proper scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown and described herein.

In the following discussion, the terms "proximal" and "distal" will be used to describe the opposing axial ends of the inventive apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient.

FIGS. 1-4 illustrate one embodiment of a wire guide exchange introducer apparatus 10 according to the present invention. The use of introducer apparatus 10 enables a physician to utilize a very small gauge needle, such as a 22, 23 or 24 gauge needle or smaller, during the initial needle insertion into the patient when initiating a medical procedure. The small gauge needle is sized such that a small diameter wire guide on the order of 0.018 inch (0.46 mm), or smaller, may be inserted through the bore of the small gauge needle. Use of the inventive apparatus enables later replacement of the small diameter wire guide with a conventional larger diameter wire guide, on the order of 0.035 to 0.038 inch (0.89 to 0.97 mm), in a manner to be described. With the larger wire guide in place, a medical device can be introduced into the vascular system over the wire guide in conventional fashion.

FIG. 1 is an elevational view illustrating an outer sleeve 12 and an inner sleeve 20 that comprise a portion of introducer apparatus 10 of the present invention. FIG. 2 is an elevational view of apparatus 10, wherein inner sleeve 20 is lockingly received within a lumen of outer sleeve 12.

In a preferred embodiment, outer sleeve 12 comprises a polymeric elongated tubular structure having a diameter in the range, e.g., of about French size 3 to 9. Outer sleeve 12 is preferably formed of radiopaque polymeric material, such as radiopaque polyethylene, although it can alternately be formed of other materials such as polytetrafluoroethylene, vinyl, nylon, polyurethane and other conventional polymers and materials that are typically used for such purposes in the medical field. Sleeve 12 is preferably configured with a slight taper at distal end 14, and terminates at distal opening 18. Distal opening 18 is significantly larger in diameter than wire guide 26 (FIG. 3), and may, for example, have a diameter of about 0.039 inch (1 mm). Outer sleeve 12 is supplied at its proximal end with a standard connector, such as Luer lock type connector 46.

Inner sleeve 20 is sized to fit freely within the lumen of outer sleeve 12. Inner sleeve 20 is generally a soft polymeric tube having a lumen therethrough. A conventional connector hub 28 which terminates into a connector, such as Luer lock connector 22, may be attached to the proximal end of inner sleeve 20. Luer lock connector 22 is configured to releasably engage and connect with Luer lock connector 46, to selectively lock outer sleeve 12 and inner sleeve 20 in the fixed longitudinal relationship with respect to each other as shown in FIG. 2. Connector hub 28 and Luer lock connector 22 preferably each have a passageway therethrough aligned with and communicating with the lumen of inner sleeve 20. Suitable connectors for medical devices are well known in the medical arts, and those skilled in the will appreciate that other known connectors between catheters, cannulae, sheaths, and related medical devices can be substituted for the Luer lock connectors described and shown herein.

When inner sleeve 20 is disposed fully within outer sleeve 12 such that connector 22 is engaged with connector 46, the tapered distal tip 24 of inner sleeve 20 extends through distal opening 18 of outer sleeve 12. As illustrated, tapered inner sleeve 20 terminates in distal opening 27. The diameter of distal opening 27 is the same as, or preferably just slightly larger than, the diameter of wire guide 26 so that small diameter wire guide 26 can pass freely therethrough. Thus, for example, when small diameter wire guide 26 has a diameter of about 0.018 inch (0.46 mm), distal opening 27 will have a diameter that is the same as or only incrementally larger than 0.018 inch (0.46 mm). The outer diameters of outer sleeve distal end opening 18 and inner sleeve distal end opening 27 need not be restricted to the exemplary diameters provided hereinabove. Rather, as will be appreciated by those skilled in the art, other appropriate combinations of diameters may be utilized to realize the benefits of the present invention for a particular use. Such combinations include diameters smaller than 0.018 (0.46 mm).

FIG. 3 is an enlarged view of the distal end of apparatus 10, and illustrates the distal end of wire guide 26. This figure more clearly illustrates the relatively smooth diametrical transition that is defined by the respective distal portions of outer sleeve 12 and inner sleeve 20 in the assembled apparatus. This relatively smooth diametrical transition essentially extends from a maximum diameter portion of outer sleeve 12, to the wire guide 26. A relatively smooth transition such as that shown in FIG. 3 enables apparatus 10 to be percutaneously inserted into the vessel over the small diameter wire guide with a minimum of trauma. This arrangement avoids the presence of larger diameter free edges that would otherwise be present at the site of the insertion when a small diameter wire guide, such as wire guide 26, is used in combination with a large diameter introducer apparatus, such as outer sleeve 12. Large diameter free edges of this type are prone to cause trauma to the patient upon introduction of the large diameter apparatus directly into the vessel.

FIG. 4 illustrates a longitudinal cross sectional view of a preferred embodiment of a fully assembled introducer apparatus 10 of the present invention. Features common to FIGS. 1-3 are represented in FIG. 4 with the same reference numerals used previously. In addition to illustrating outer sleeve 12 and inner sleeve 20 as before, FIG. 4 also illustrates inner stiffening cannula 30. Stiffening cannula 30 maybe a thin stainless hypodermic needle cannula as described previously. Alternatively, stiffening cannula 30 can be formed from other conventional biocompatible materials that have sufficient rigidity to provide support for the inner sleeve, and that do not add significant bulk to the overall apparatus. Preferably, distal end portion 31 of stiffening cannula 30 terminates at a point proximal to tapered distal portion 24 of inner sleeve 20. As shown in FIG. 4, tapered distal portion 24 is drawn and tapered such that it shields the distal end portion 31 of stiffening cannula 30.

Unlike the prior art arrangement, in the inventive apparatus depicted in FIG. 4, the inner sleeve 20 and the stiffening cannula 30 are bonded together or otherwise fixedly engaged along at least a portion of their respective lengths such that relative axial movement between them is inhibited. Preferably, such bonding or engagement includes at least a distal portion of inner sleeve 20 and stiffening cannula 30. As a result, the distal tip 24 of inner sleeve 20 is inhibited from folding or otherwise retreating in the proximal direction when an obstruction is encountered upon insertion of the apparatus. Thus, distal tip 24 continues to cover, or "shield", stiffening cannula distal end 31. If the shield was not maintained in this manner, the distal end of the rigid stiffening cannula may protrude through inner sleeve distal end 27 as the inner sleeve is urged backwardly (i.e, in the proximal direction) when it encounters an obstruction upon insertion into the vasculature. The affected vessel and tissue would then be directly exposed to the rigid stiffening cannula, thereby causing trauma to the vessel and/or tissue.

Figure 7:
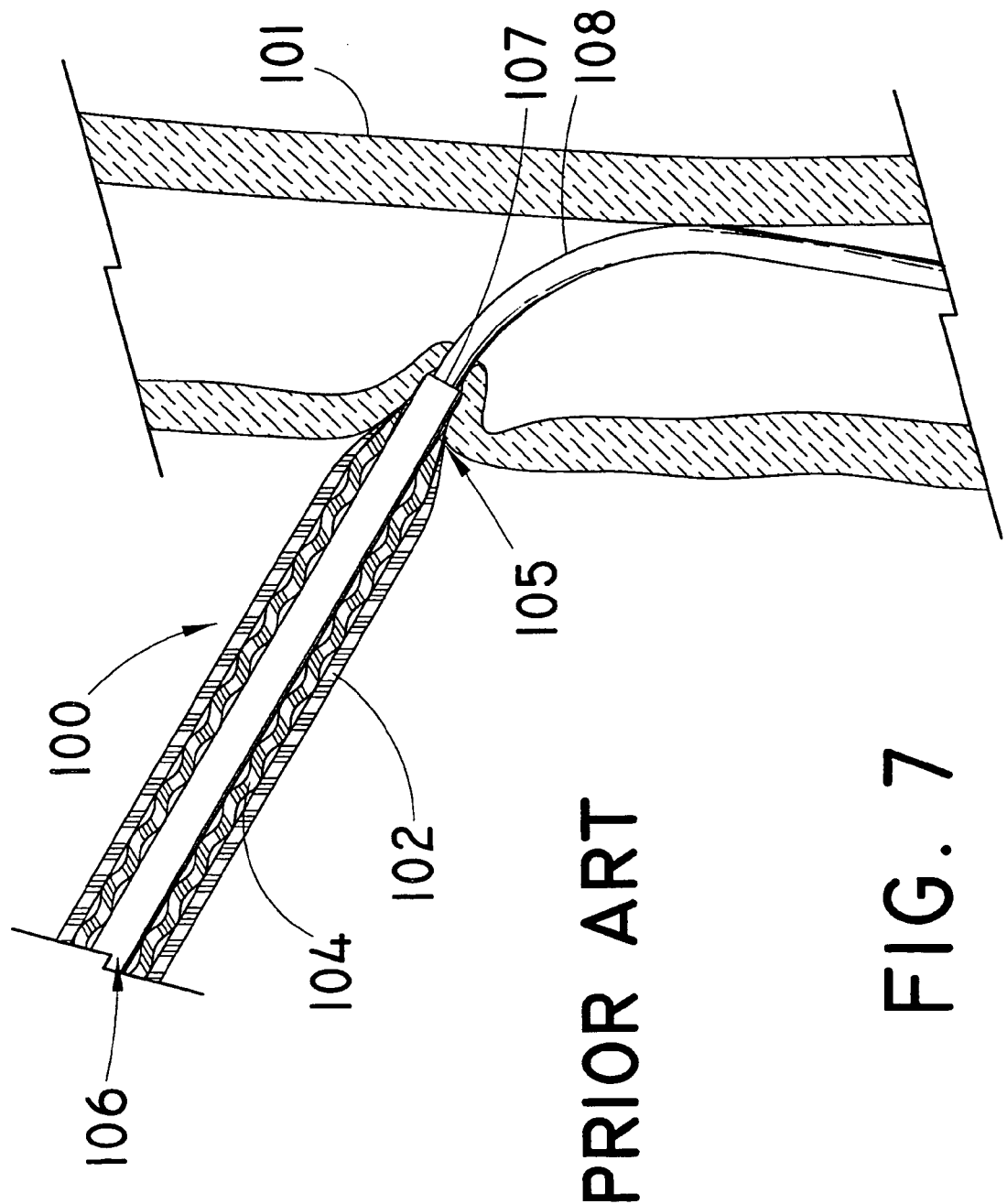
FIG. 7 is a longitudinal view, partially in section, of a prior art introducer apparatus showing the accordioning of the inner sleeve when resistance is encountered during insertion of the prior art apparatus.

For purposes of comparison, FIG. 7 illustrates a longitudinal view, partially in section, of a prior art introducer apparatus 100. Prior art apparatus 100 also includes an outer sleeve 102, an inner sleeve 104 and a stiffening cannula 106 as described herein. Wire guide 108 passes through the lumen of the stiffening cannula 105. As with the inventive apparatus, prior to an encounter with an obstruction during insertion, the polymeric distal tip 105 of inner sleeve 104 is initially drawn and tapered in a manner such that the distal end of the hard, stiffening cannula 106 is fully covered by the body of the inner sleeve 104, and the distal end 105 of the inner sleeve projects in the distal direction beyond the distal end of outer sleeve 102. However, upon insertion of prior art apparatus 100 into a body vessel 101 as shown in FIG. 7, distal tip 105 of inner sleeve 104 may encounter resistance from obstructions, such as tough fibrous tissue. In this event, the body of the inner sleeve 104 is forced backwardly in the proximal direction, or "accordioned", back on the stiffening cannula 106, as shown. As the inner sleeve 104 retreats in the proximal direction, the opening at the distal tip 105 of the inner sleeve expands to expose the previously-shielded distal end 107 of stiffening cannula 105. This action is undesirable because the exposed distal end of the higher durometer stiffening cannula comes into direct contact with the vessel and/or tissue, which may cause significant trauma to the affected vessel and/or tissue.

In contrast to the prior art arrangement illustrated in FIG. 7, inner sleeve 20 and stiffening cannula 30 of the present invention are engaged in a manner such that relative axial movement between the respective distal portions of the inner sleeve and the stiffening cannula is substantially inhibited. As a result, distal end 31 of stiffening cannula 30 remains shielded by the distal end of inner sleeve 20. Preferably, the inner sleeve and the stiffening cannula are engaged in a manner such that relative axial movement between them is prevented altogether.

In a preferred embodiment, axial movement between the inner sleeve 20 and the stiffening cannula 30 is inhibited by forming a joint, such as a mechanical joint, between the inner sleeve and the stiffening cannula. One preferred method for forming a suitable joint between inner sleeve 20 and stiffening cannula 30 is by establishing a bond, such as a thermal bond, between the inner surface of inner sleeve 20 and the outer surface of stiffening cannula 30. Those skilled in the art will appreciate that alternative joinder means, including but not limited to the use of bonding agents or adhesives, can be utilized to form the attachment between the inner sleeve and the stiffening cannula. The use of bonding agents or adhesives is generally considered a less desirable option than thermal bonding. These techniques often require the use of agents, such as a cyanoacrylate or epoxy, which must be carefully monitored to prevent contact with the patient's blood. In addition, use of such agents adds an element of bulk and wall thickness to the device not present when the inner sleeve is thermally bonded to a roughened outer surface of the stiffening cannula as described.

Those skilled in the art can readily select appropriate materials for the inner sleeve and the stiffening cannula that are suitable for the purposes described herein, and that are amenable to the formation of a reliable bond therebetween. Preferably, the inner sleeve 20 is formed from a conventional polymer well known for such use in introducer apparatuses, such as a nylon or polyethylene. The inner sleeve preferably has an inner diameter that is the same, or only slightly larger, than the outer diameter of the stiffening cannula 30. The stiffening cannula should be formed of a material that provides stiffness and yet is also capable of having a thin wall, so as to not add appreciably to the overall diameter of the cannula. Preferably, the stiffening cannula comprises a relatively stiff polymer, such as PET, or a metal such as stainless steel. Alternatively, relatively hard metallic alloys, such as nitinol, and fiber composite materials may be substituted.

One preferred method of bonding the inner sleeve 20 to the stiffening cannula 30 is described below:
1. Initially, a polymeric stiffening cannula of an appropriate length is cut and de-burred. Typical lengths may be in the range of 5 cm to 25 cm, with 8 cm to 10 cm being preferred. Typical cannula diameter may be 20 to 25 gauge thin wall cannula. The precise length and gauge size will, of course, vary depending upon the respective lengths and gauge sizes of the inner and outer sleeves.
2. The outside surface of the stiffening cannula is roughened along its outer circumference to form circumferential irregularities on the surface. This may be accomplished in various well-known ways, such as by spinning the cannula in a lathe, and applying a medium to course grit (such as 40 to 80 grit (430 to 165 microns)) abrasive cloth to the spinning cannula.
3. A small flare may be formed at the proximal end of the cannula with a suitable flaring tool, and the distal end may be rounded smooth by such techniques as buffing or fine grit grinding.
4. A close fitting inner sleeve is positioned over the stiffening cannula so that the proximal end of the inner sleeve butts against the flared portion of the stiffening cannula, and the distal end of the inner sleeve extends a distance of about 5 to 10 mm beyond the distal end of the stiffening cannula.

5. A close-fitting heat shrink tube formed of a conventional heat shrink material, such as PTFE, is positioned over the entire assembly such that the shrink tube extends 1 or 2 cm beyond both ends of the assembly.

6. The assembly is exposed to heat by conventional heating means, such as a heat gun, a torch, an oven or other suitable means. This causes portions of the inner sleeve to melt and flow into the circumferential irregularities on the surface of the roughened stiffening cannula. The PTFE shrink tube typically shrinks at about 400 to 450° F. (204 to 232° C.). The heat is maintained until the PTFE shrink tube fully shrinks, thereby melting the polymeric body of the inner sleeve and forcing it into tight contact with the roughened outer surface of the stiffening cannula.

7. The assembly is cooled, and a notch is formed at one end of the shrink tube. The shrink tube is then split at the notch and removed from the assembly, leaving the inner sleeve heat bonded to the stiffening cannula.

8. The distal tip of the inner sleeve is trimmed and formed such that it tapers to the small wire guide diameter desired, e.g., 0.014 to 0.018 inch (0.36 to 0.46 mm). The tapered tip may be formed in conventional manner, such as by inserting the polymeric distal tip of the inner sleeve into a heated tapered mold. The distal end of the stiffening cannula is proximal to the distal tip of the inner sleeve about 1 or 2 mm.

9. A suitable fitting, such as a standard medical luer fitting, is attached to the proximal end of the inner sleeve by conventional means, such as by gluing or insert molding, thereby capturing both the polymeric sleeve and the stiffening cannula.

The dimensions and conditions provided hereinabove are exemplary for the particular example described, and are not intended to be limiting in any manner. The remainder of the apparatus may be formed in a conventional manner. For example, the tip taper of the outer sleeve may also be formed in a heated tapered mold in the same manner as the inner sleeve. The outer sleeve and the inner sleeve are preferably formed such that when they are locked or otherwise joined altogether, the distal tip of the outer sleeve 12 generally ends where the tip taper 24 of inner sleeve 20 begins. In this way, the distal tip of introducer apparatus 10 appears to have a continuous distal tip taper.

By bonding or otherwise engaging the melted inner sleeve to the roughened outer surface of the stiffening cannula, relative axial movement between them is inhibited. As a result, when the tapered tip of the inner sleeve encounters resistance, the inner sleeve is held in place, and resists the tendency to accordion with respect to the stiffening cannula as shown in the prior art device of FIG. 7.

Another alternative way of forming the engagement between the inner sleeve 20 and the stiffening cannula 30 is by combining two separate engagement methods. Thus, the above-described thermal bonding method may be combined with another engagement method, such as adhesion. In this case, the inner sleeve and the stiffening cannula may be glued together along their length and subjected to thermal bonding. In another alternative, the use of glue may be particularly effective when combined with the circumferential roughening of the stiffening cannula surface, but in the absence of the thermal bonding. In this alternative, the roughened surface of the stiffening cannula may be coated with a UV light curable glue. A snug fitting inner polymeric sleeve that is translucent or transparent to light can then be slipped over the stiffening cannula. The assembly is then exposed to a UV light source to cure the adhesive. This method has the advantage of eliminating the need for utilizing a heat shrink tube for each product.

In one embodiment, the inner sleeve 20 can be formed of PTFE. Since PTFE has a low coefficient of friction, it can pass more easily through tough tissues and has an appropriate flexibility and softness for the tip taper. Furthermore, the interior of the PTFE sleeve can be chemically treated to provide an etched surface for improving attachment of the inner sleeve to the roughened stiffening cannula 30.

In yet another variation, the polymeric sleeve covering the stiffening cannula can itself comprise the heat shrink tube that remains on the stiffening cannula. Many different polymers with different stiffness properties, such as PTFE, nylon, polyethylene, etc., can be fabricated as an appropriate heat shrink tube for use as the polymeric inner sleeve. In this case, the shrinkable polymeric inner sleeve is able to grip the roughened stiffening cannula sufficiently to prevent the accordion effect. This alternative also eliminates the extra manufacturing step associated with the removal of the heat shrink tube.

One exemplary manner of use of the inventive apparatus is described hereinafter. Initial entry is made into a body vessel with a conventional small gauge needle. FIG. 6 illustrates one type of needle 40 that may be utilized for the initial entry into the vessel. Preferably, needle 40 is a thin wall needle and has a gauge size of 22-24 gauge, or smaller. As stated previously, a 22 gauge needle typically has an O.D. of about 0.028 inch (0.71 mm), and an I.D. of about 0.19 inch (0.48 mm). Small gauge needles, such as needle 40, not only have a smaller diameter than larger gauge needles, but also normally have a shorter bevel 41 at the needle tip. Such small gauge needles are considered small enough to not cause damage to tissue or organs upon insertion, and the shorter bevel facilitates insertion into the lumen of a small vessel when compared with a larger beveled needle.

A small diameter wire guide 26 is percutaneously inserted into the vessel through the bore of the needle according to, e.g., the well-known Seldinger technique. Preferably, the wire guide will have a diameter substantially the same as, or incrementally smaller than, the diameter of the open tapered distal end of the inner sleeve so that the wire guide can pass freely therethrough. As a result, a generally smooth diametrical transition is provided between the distal end of outer sleeve 12 and wire guide 26. Preferably, these diameters will not exceed about 0.018 inch (0.46 mm). With smaller gauge needles, such as 23 gauge, 24 gauge or smaller, the diameter may be correspondingly less than 0.018 inch (0.46 mm), such as 0.016 inch (0.41 mm), 0.14 inch (0.36 mm), or smaller. The inventive wire guide exchange apparatus 10 is slowly introduced into the vessel over the wire guide until outer sleeve 12 penetrates the vessel. Since the stiffening cannula and the inner sleeve are engaged, such as by bonding, relative axial movement between them is substantially prevented as tapered distal portion 24 of inner sleeve 12 penetrates any tough, fibrous tissue that may be encountered as the inner sleeve enters the vessel. As a result, inner sleeve tapered distal portion 24 continues to shield the distal end of hard stiffening cannula 30, even during passage through such tough, fibrous tissue. After the outer sleeve portion 12 of introducer apparatus 10 has penetrated the vessel, wire guide 26, inner sleeve 20 and stiffening cannula 30 may be withdrawn from the vessel, leaving outer sleeve 12 in place in the vessel. Other details of the insertion of a large diameter outer sleeve via a small diameter wire guide not directly relevant to the above discussion are provided in the incorporated by reference U.S. Pat. No. 4,650,472.

Figure 5:
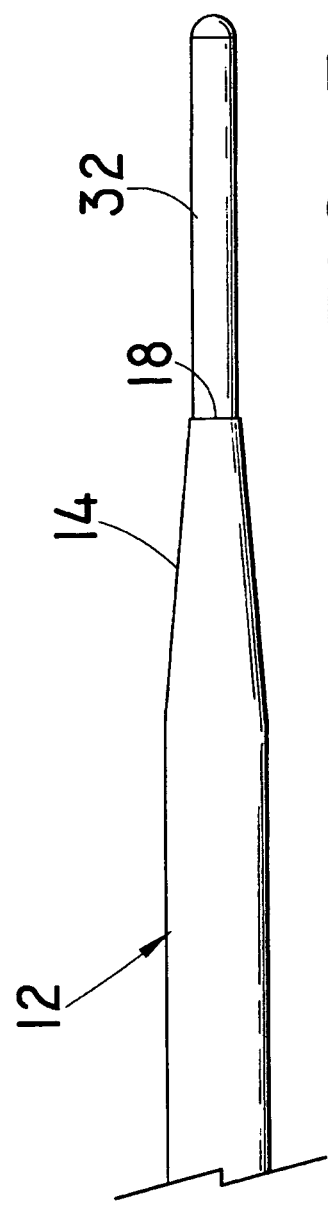
FIG. 5 is an enlarged elevational view of the distal portion of the inventive apparatus, following withdrawal of the inner sleeve and stiffening cannula, and insertion of a larger diameter wire guide.

A larger diameter wire guide 32, preferably on the order of 0.35 to 0.38 inch diameter (0.89 to 0.97 mm) may then be introduced into the vessel through outer sleeve 12. This arrangement is shown in FIG. 5. Preferably, the diameter of outer sleeve distal end 18 is virtually the same, or only incrementally larger, than diameter of the wire guide. As a result, wire guide 32 is freely movable through outer sleeve 12, and a generally smooth transition is provided from the distal portion 14 of the outer sleeve to wire guide 32. The outer sleeve may then be removed, leaving larger diameter wire guide 32 in place in the vessel. Wire guide 32 is then in position to accept a catheter or other interventional device for insertion into the vessel. Further details of this procedure not directly relevant to this discussion are provided in the article "Interventional Access with Thin Needle Technique", R. A. Neff, *Journal of Interventional Radiology* (1986) 1, 41-42, incorporated by reference herein.

The present invention also comprises an introducer system for providing access to a body vessel of a patient. The introducer system comprises introducer apparatus 10, and also includes one or more of smaller diameter wire guide 26 and larger diameter wire guide 32. As a further option, a small gauge needle may also be included in the introducer system. Preferably, the small gauge needle has a gauge size of 22-24 gauge, or smaller, and is of conventional thin wall construction.

When utilizing the teachings of the present invention, those skilled in the art may readily select other appropriate combinations of materials for inner sleeve 20 and stiffening cannula 30 for a particular use. Similarly, those skilled in the art may readily determine other appropriate means of joining such materials. All such materials, and methods for joining the same, are considered within the scope of the present invention.

It is therefore intended that the foregoing detailed description be regarded as illustrative rather than limiting, and that it be understood that it is the following claims, including all equivalents, that are intended to define the spirit and scope of this invention.

The invention claimed is:

1. An apparatus for providing percutaneous access to a vessel of a patient over a wire guide, comprising:
   an outer sleeve having proximal and distal open ends, and having a lumen extending longitudinally therethrough;
   an inner sleeve having proximal and distal open ends, and having a lumen extending longitudinally therethrough, said inner sleeve having said proximal and distal open ends being receivable within the lumen of said outer sleeve and selectively removable therefrom, said inner sleeve having a main body portion and having a distal portion that tapers toward the inner sleeve distal open end, said tapered distal portion extending distal to the distal open end of said outer sleeve when said inner sleeve is received in said outer sleeve lumen to provide a generally smooth diametrical transition between said outer sleeve and said wire guide; and
   a stiffening cannula having proximal and distal open ends, and having a lumen extending longitudinally therethrough, the lumen of said stiffening cannula sized to receive said wire guide therethrough, said stiffening cannula being sized to be received within the lumen of said inner sleeve and extending along the main body portion of the inner sleeve to a terminal point, said terminal point being proximal to the inner sleeve distal end, said stiffening cannula and said inner sleeve being engaged such that relative axial movement between said inner sleeve and said stiffening cannula is substantially inhibited, wherein said inner sleeve distal portion shields said stiffening cannula distal end when said apparatus is percutaneously introduced into said vessel.

2. The apparatus of claim 1, wherein said inner sleeve and said stiffening cannula are engaged by bonding a length of said inner sleeve and a length of said stiffening cannula.

3. The apparatus of claim 1, wherein said stiffening cannula has a roughened outer surface, and said inner sleeve and said stiffening cannula are engaged by thermal bonding of said inner sleeve to said roughened outer surface of said stiffening cannula.

4. The apparatus of claim 1, wherein said inner sleeve and said stiffening cannula are engaged by adhesion.

5. The apparatus of claim 1, wherein said terminal point of said stiffening cannula is between about 1 and 2 mm proximal of the distal open end of the inner sleeve.

6. The apparatus of claim 1, wherein said stiffening cannula and said inner sleeve are engaged in a manner such that relative axial movement therebetween is prevented.

7. The apparatus of claim 1, wherein said outer sleeve has a main body portion and has a distal portion that tapers toward the outer sleeve distal open end, said tapered distal portion corresponding with the tapered distal portion of the inner sleeve in a manner such that a generally smooth diametrical transition is defined between said outer sleeve tapered portion and said wire guide.

8. The apparatus of claim 1, wherein said terminal point is positioned at a point proximal to said inner sleeve tapered distal portion.

9. The apparatus of claim 1, wherein said outer sleeve distal open end has a diameter of at least about 0.89 mm, and said inner sleeve distal open end has a diameter not exceeding about 0.46 mm.

10. A system for providing percutaneous access to a vessel of a patient, comprising:
    a first wire guide, said first wire guide having a diameter;
    a second wire guide, said second wire guide having a diameter; and
    an introducer apparatus comprising an outer sleeve having proximal and distal open ends and a lumen extending longitudinally therethrough; said distal open end having a diameter substantially the same as the diameter of the second wire guide and sized to permit said second wire guide to pass freely therethrough; an inner sleeve having a lumen extending longitudinally therethrough and having a distal portion that tapers to an open distal end, said inner sleeve removably received within the lumen of said outer sleeve, the open distal end of said inner sleeve having a diameter substantially the same as the diameter of the first wire guide and sized to permit said first wire guide to pass freely therethrough; and a stiffening cannula having a lumen extending longitudinally therethrough, the lumen of said stiffening cannula sized to receive said first wire guide therethrough, said stiffening cannula being sized to be received within the lumen of said inner sleeve, the stiffening cannula and the inner sleeve being engaged such that relative axial movement therebetween is substantially inhibited whereby said stiffening cannula is removable from said outer sleeve upon removal of inner sleeve having said open distal end, and oriented such that said tapered distal portion shields said stiffening cannula when said apparatus is percutaneously introduced into said vessel.

11. The system of claim 10, wherein a distal portion of said outer sleeve tapers toward said open distal end of said removable outer sleeve, said outer sleeve tapered portion corresponding with the tapered distal end of the inner sleeve such that a generally smooth diametrical transition is defined between said outer sleeve tapered portion and said wire guide.

12. The system of claim 10, wherein said first wire guide diameter does not exceed about 0.18 inch (0.46 mm), said second wire guide diameter is between about 0.035 and 0.038 inch (0.89 to 0.97 mm), and said outer sleeve distal open end diameter is about 0.039 inch (1.0 mm).

13. The system of claim 10, further comprising a needle, said needle having an inner bore not exceeding about 0.018 inch (0.46 mm).

14. The apparatus of claim 1, wherein said inner sleeve comprises an elongated polymeric member extending from said inner sleeve proximal end to said distal sleeve open end, such that said elongated polymeric member and stiffening cannula are capable of being withdrawn from said outer sleeve lumen when said apparatus is percutaneously introduced into said vessel.

\* \* \* \* \*